United States Patent [19]

Dahl et al.

[11] Patent Number: 4,670,246

[45] Date of Patent: Jun. 2, 1987

[54] MICROENCAPSULATED PYRETHROIDS

[75] Inventors: Gerd H. Dahl, Radnor Township, Delaware County, Pa.; Joseph Simkin, Miami, Fla.

[73] Assignee: Pennwalt Corporation, Philadelphia, Pa.

[21] Appl. No.: 726,735

[22] Filed: Apr. 24, 1985

Related U.S. Application Data

[63] Continuation-in-part of Ser. No. 668,231, Nov. 5, 1984, abandoned.

[51] Int. Cl.⁴ .................. A61K 9/50; A01N 25/00
[52] U.S. Cl. ........................424/419; 514/963
[58] Field of Search .................. 424/19, 32, 33; 514/963

[56] References Cited

U.S. PATENT DOCUMENTS

| | | | |
|---|---|---|---|
| 3,575,882 | 4/1971 | Vandegaer et al. | 424/32 |
| 3,577,515 | 5/1971 | Vandegaer | 424/32 |
| 3,959,464 | 5/1976 | DeSavigny | 424/32 |
| 4,107,292 | 8/1978 | Nemeth | 424/32 |
| 4,155,741 | 5/1979 | Scher et al. | 424/32 |
| 4,280,833 | 7/1981 | Beetsman et al. | 424/32 |
| 4,409,201 | 10/1983 | Heinrich et al. | 424/32 |
| 4,497,793 | 2/1985 | Simkin | 424/32 |
| 4,656,610 | 11/1977 | Barber, Jr. et al. | 424/32 |

FOREIGN PATENT DOCUMENTS 54-55726  5/1979  Japan ............................ 424/32

OTHER PUBLICATIONS

Das Controlled Release Technology: Bioengineering Aspects.
CA 91:187,926a, Alternative Formulations of Synthetic Pyrethroids.

*Primary Examiner*—Shep K. Rose

[57] ABSTRACT

A sprayable insecticidal composition of low fish toxicity of a mixture in water of microcapsules comprised of a pyrethroid (synthetic pyrethrin) contained within an encapsulating wall of a cross-linked polymeric material, and methods of preparation and method of use of the composition on a wide variety of crops and aquatic sites infested with a broad spectrum of undesirable insects.

6 Claims, No Drawings

MICROENCAPSULATED PYRETHROIDS

CROSS-REFERENCE TO RELATED APPLICATIONS

This application is a continuation-in-part of U.S. patent application Ser. No. 668,231, filed Nov. 5, 1984, now abandoned.

BACKGROUND OF THE INVENTION

The use of pyrethroids (synthetic pyrethrins) for the control of agricultural insect pests on crops has dramatically increased in recent years. As a class of compounds, they are by far the most rapidly growing group of insecticides and are expected to capture within a few years as much as half of the total insecticide market. Their advantages are a high degree of insecticidal activity and, generally, low mammalian toxicity when compared to other insecticides, e.g., organophosphates. A serious disadvantage is their high fish toxicity which severely limits their use on crops grown in or near water, as for example rice (control of rice water weevil).

Microencapsulation as a technique for formulating pesticides has been applied to organophosphate insecticides, such as diazinon and methyl parathion, and the resultant products are commericalized for agricultural and structural pest-control uses as KNOX OUT® 2FM insecticide and PENNCAP® M insecticide (Registered Trademarks of Pennwalt Corporation), respectively. This technique has been shown to impart lengthened biological effectiveness to these pesticides and to reduce their mammalian toxicity. Thus, it has been found that KNOX OUT® 2FM insecticide is more than 16 times less toxic orally and more than 8 times less toxic dermally than conventional formulations of the diazinon active ingredient. Similarly, PENNCAP® M insecticide is at least 5 times less toxic orally and 10 times less toxic dermally than conventional formulations of the unencapsulated methyl parathion active ingredient. Thus, microencapsulation can be expected to generally reduce mammalian toxicity by a factor of 5 to ca. 20 times. On the other hand, fish toxicity of methyl parathion as measured by 96-hour exposure to trout in standard tests is virtually unaffected by microencapsulation. Thus, in this test the concentrations of active ingredient required to kill 50% of the fish are 6.44 ppm and 5.16-8.19 ppm for the encapsulated and conventional methyl parathion formulations, respectively.

Quite unexpectedly, it has been discovered that the microencapsulation of pyrethroids results in a reduction of fish toxicity that far exceeds the above-mentioned values. Thus, in a 96-hour exposure of trout to water containing an unencapsulated, emulsifiable-concentrate of pyrethroid (permethrin), 0.015 mg of the active ingredient per liter of water resulted in the death of 50% of the fish present. In contrast, none of the trout exposed to the encapsulated permethrin formulation died, even at the highest concentration, 18.5 mg of active ingredient per liter. The difference in acute toxicity is, thus, in excess of 1,200-fold. In another test using a different formulation of microencapsulated permethrin, the difference between concentrations required to cause 50% of the fish to die was 4,800-fold. This dramatic reduction in fish toxicity, therefore, exceeds by far the previously observed decrease in toxicity that is typical for microencapsulated organophosphates.

While no satisfactory explanation has been found for this unexpectedly low fish toxicity, these microencapsulated pyrethroids, such as permethrin, have excellent biological activity against target insect species while maintaining a low level of mammalian toxicity.

This unexpected discovery has important economic consequences in that these increasingly important insecticides are now useful in applications for which they are currently not approved for use due to high fish toxicity.

BRIEF SUMMARY OF THE INVENTION

The process of manufacture of the invention is defined as a process of encapsulation by interfacial condensation of complementary, organic polycondensate-forming intermediates reacting to form polycondensate selected from the group consisting of polyamide, polyamide-polyurea, polysulfonamide, polyester, polycarbonate, polyurethane and polyurea, comprising (1) establishing by agitation, a dispersion of to-be-encapsulated synethetic pyrethroid droplets containing a first of said intermediates, in a body of liquid which is in continuous phase and is immiscible with the droplets and is essentially free of any reactant complementary to said first intermediate, and (2) thereafter bringing a second of said intermediates, that is complementary to the first intermediate, into the continuous liquid phase so that the first and second intermediates react at the interfaces between the droplets and the continuous phase to encapsulate the droplets within a skin of said selected polycondensate, at least one of said first and second intermediates comprising at least in part a polyfunctional reactant which (a) is complementary to and effective for cross-linking reaction with the other of said first and second intermediates and (b) has "an average of more than two reactive groups" (as discussed below) that are the same as each other and are effectively functional in said selected polycondensate-forming reaction and are selected from the class consisting of amine, hydroxy, isocyanate, —COCl, and —SO$_2$Cl groups, said first and second intermediates thereby reacting to encapsulate the droplets within the aforesaid polycondensate skin having cross-linkage therein.

The above polycondensate-forming intermediates include either a single monomer or a mixture of monomers, as appropriate. The useful commercially available monomers generally comprise a mixture of monomers having two, three, or more reactive groups per monomeric unit. Such mixtures may have an average of between 2 and 3 or more reactive groups; they are considered as having an average of more than two such reactive groups for the purpose of this discussion.

The preferred pyrethroids for encapsulation are: allethrin, dimethrin, resmethrin, tetramethrin, cypermethrin, bioresmethrin, phenothrin, permethrin, biopermethrin, decamethrin, fenvalerate, fluvalinate, and barthrin.

The insecticidal composition of the invention is defined as a storage-stable, sprayable, aqueous-based insecticidal composition consisting essentially of a mixture in water of microcapsules comprised of a pyrethroid contained within an encapsulating wall of a cross-linked polymeric material selected from the group consisting essentially of polyamide-polyurea, polyamide, polysulfonamide, polyester, polycarbonate, polyurethane, and polyurea, the pyrethroid being diffusible therethrough, about 10 to 100% of the cross-linked polymeric encapsulating wall being embodied in a three dimensional polymer network, the weight ratio of said pyrethroid to the polymer of the microcapsule being in the range of about 1:1 to 50:1, and the concentration of the microcapsules in the aqueous mixture being from about 1 to about 30% by weight. The preferred pyrethroids are listed as above for the process of the invention.

The method of use of the invention is defined as applying an insectically effective amount of the above composition (typically, from at least about 0.02 to about 0.25 lbs. of active ingredient per acre, or higher) to an insect infested crop to control the undesirable insects. The crops include: rice, almonds, apples, celery, broccoli, brussels sprouts, cabbage, cauliflower, cotton, lettuce, peaches, pears, potatoes, soybeans, spinach, sweet corn, and forests; and the undesirable insects include rice water weevil, green rice leafhopper, brown planthopper, white-backed planthopper, grass leaf roller, rice stem borer, smaller brown planthopper, mosquito, navel orangeworm, peach twig borer, apple aphid, redbanded leafroller, obliquebanded leafroller, plum curculio, white apple leafhopper, spotted tentiform leafminer, tarnished plant bug, vegetable leafminer, cabbage looper, imported cabbageworm, granulate cutworm, black cutworm, fall armyworm, beet armyworm, diamondback moth, bollworm (corn earworm), tobacco budworm, pink bollworm, lygus bugs, cotton leaf perforator, boll weevil, cotton fleahopper, saltmarsh caterpillar, whitefly, cotton aphid, oriental fruit moth, green fruitworm, lesser peachtree borer, rose chafer, pear psylla, codling moth, green fruitworm, Colorado potato beetle, potato leafhopper, aster leafhopper, potato flea beetle, potato aphid, potato tuberworm, potato psyllid, green cloverworm, Mexican bean beetle, bean leaf beetle, soybean looper, velvetbean caterpillar, leafhoppers, cutworm complex, European corn borer, Southern armyworm, gypsy moth, western spruce budworm, eastern spruce budworm, tussock moth, tent caterpillar, fall webworm, canker worm, and pine sawfly.

The method of use also includes controlling mosquitos by applying an insecticidally effective amount of the above composition to water in which the mosquitos or mosquito larvae breed, hatch, develop, and live.

DETAILED DESCRIPTION OF THE INVENTION

Methods for microencapsulating droplets, including insecticides generally, are described in U.S. Pat. No. 3,577,515 to Vandegaer (issued May 14, 1971) and U.S. Pat. No. 3,959,464 to De Savigny (issued May 25, 1976). The above methods are, generally, suitable for preparing the microencapsulated product of this invention by substituting the pyrethroid for the droplets to be encapsulated. These processes, however, do not work with natural pyrethrins. The teachings of the above patents, in this regard, are incorporated herein by reference.

Thus, a mixture of the pyrethroid and polymer precursors, such as sebacoyl chloride and polymethylene polyphenylisocyanate, are brought into contact in the form of an emulsion with an aqueous mixture of caustic and divalent and/or polyfunctional amines. After neutralization, the resultant aqueous suspension of microcapules is stabilized by the addition of one or more suitable suspending agents.

Insecticidal properties (biological efficacy) of such a formulations are typically determined in laboratory tests using houseflies as the test organism. The efficacy test is described as follows:

Glass plates (approximately 65 square inches in area) are sprayed with 0.20 mg of the composition to be tested per square foot. The plates are then allowed to age 30 days after being placed in approximately one-cubic-foot screened cubical cages at room temperature. Adult, mixed-sex house flies (*Musca domestica*, NAIDM strain, average of 44 per cage) are then introduced at time intervals as given in the table into each container along with food (powdered milk and sugar) and water. The tests are run in duplicates. Evaluations of mortality are made after exposure for 24 hours.

The fish toxicity of microencapsulated and conventional emulsifiable concentrate formulations of pyrethroids are determined by a standard protocol. In this procedure, the required pesticide concentrations are added to 15 liters of water of known water quality. After proper dispersion of the pesticide, rainbow trout fingerling are added. The tests are performed simultaneously at 12° C. and last 96 hours. Lighting is maintained at intervals of 16 hours of light followed by 8 hours of darkness. Mortality readings are taken at 24, 48, 72, and 96 hours.

The pyrethroids are well known and are commercially available and/or their preparation descibed in the literature. Suitable pyrethroids include (followed by CAS registry no., where known): allethrin (584-79-2), dimethrin (70-38-2), resmethrin (10453-86-8), bioresmethrin (28434-01-7), phenothrin (26002-80-2), permethrin (52645-53-1), biopermethrin (28434-01-7), decamethrin (52820-00-5), fenvalerate (51630-58-1), barthrin (70-43-9), tetramethrin, cypermethrin, and fluvalinate, among others.

Structural formulas for some of the preferred pyrethroids are set forth in the parent application Ser. No. 668,231, filed Nov. 5, 1984 (now abandoned) at page 9.

The present invention provides an improved insecticidal composition, having the advantages and alleviating the problems as above discussed, comprising microcapsules of a synthetic pyrethroid contained within an encapsulating wall or skin of cross-linked polymeric material. A preferred embodiment of the invention is the admixture of the microcapsules in an aqueous carrier, i.e., a slurry, suspension, or dispersion of the microcapsules in water, which may have included therein suspending agents, for example, cross-linked acrylic acid interpolymers as discussed in U.S. Pat. No. 3,426,004, other suspending agents such as hydroxyethyl cellulose, gums, clays, sub-micron size silica and other inorganic materials; wetting agents and dispersants such as detergents, polyvinyl alcohols, gelatin, methyl cellulose, casein and clays; and "stickers" (materials which will cause the capsules to stick onto the foilage and not drop to the ground) such as gelatin, bentonites, gums, polysulfides, polyacrylic acid, and both petroleum, plant, and animal oils.

The polymerization method and technique of preparing the polymeric skin of the microcapsules, generally, embodied in this invention are described in the patent of J. E. Vandegaer, U.S. Pat. No. 3,577,515, May 4, 1971, and the corresponding British Pat. No. 1,091,141, published Nov. 15, 1967 (the teachings of which are incorporated herein by reference). Described in these references is a process of encapsulation by interfacial condensation of complementary, organic, polycondensate-forming intermediates which react to form cross-linked, polycondensate which comprises: establishing, by agitation, a dispersion of to-be-encapsulated droplets containing a first of said intermediates, in a body of liquid which is in continuous phase and is immiscible with the droplets and is essentially free of any reactant complementary to said first intermediate, and (2) thereafter bringing a second of said intermediates, i.e., complementary to the first intermediate, into the continuous liquid phase so that the first and second intermediates react as interfaces between the droplets and the continuous phase to encapsulate the droplets with a skin of said polycondensate, at least one of said first and second intermediates (either or both of which may be mixtures of monomers) comprising at least in part a polyfunctional reactant which (a) is complementary to and effective for cross-linking reaction with the other of said first and second intermediates and (b) has at least three reactive groups that are the same as each other and are effectively functional in said polycondensate-forming reaction, and that are selected from the class consisting of amine, isocyanate, —COCl and —SO$_2$Cl groups, said first and second intermediates thereby reacting to encapsulate the droplets within the aforesaid polycondensate skin having cross-linking therein. Examples of suitable diamine and polyamine reactants are ethylene diamine, phenylene diamine, toluene diamine, hexamethylene diamine, diethylene triamine, piperazine, 1,3,5-benzenetriamine trihydrochloride, 2,4,6-triaminotoluene trihydrochloride, tetraethylene pentamine, pentaethylene hexamine, polyethylene imine, 1,3,6-triaminonaphthlene, 3,4,5-triamino-1,2,4-triazole, melamine, and 1,4,5,8-tetraminoanthraquinone. Examples of difunctional and polyfunctional acid derived compounds providing —COCl and —SO$_2$Cl reactive groups are sebacoyl chloride, ethylene-bis-chloroformate, phosgene, azelaoyl chloride, adipoyl chloride, terephthaloyl chloride, dodecanedioic acid chloride, dimer acid chloride, 1,3-benzene sulfonyl dichloride, trimesoyl chloride, 1,2,4,5-benzene tetraacid chloride, 1,3,5-benzene trisulfonyl chloride trimer acid chloride, citric acid chloride and 1,3,5-benzene trischloroformate. Intermediates useful in providing reactive isocyanate groups are represented by such compounds as paraphenylene diisocyanate, meta-phenylene diisocyanate, naphthalene-1,5-diisocyanate, tetrachloro-m-phenylene diisocyanate, 2,4-toluene diisocyanate, 2,6-toluene diisocyanate, 4,4-diphenyl diisocyanate, the dichloro diphenyl methane diisocyanates, bibenzyl diisocyanate, bitolylene diisocyanate, the diphenyl ether diisocyanates, the dimethyldiphenyl diisocyanates, the polymethylene polyphenyl isocyanates, triphenylmethane-4,4',4''-triisocyanate, isopropylbenzene α-diisocyanate and the like.

Sufficient polyfunctional reactant (i.e., trifunctional or greater), e.g., a reactant having at least 3 functional groups thereon as above-described, is provided in the polycondensation recipe to produce microcapsules wherein the polyamide-polyurea capsule wall is about 10 to 100% cross-linked, that is 10 to 100% of the polymer is part of a three dimensional polymer network. In the preferred embodiments the polyamide-polyurea capsule wall will be 30 to 90% cross-linked. Microcapsules of polyamides with no cross linking would, graphically speaking, be made up of strands of linear polymer molecules not connected to each other. By cross linking the polyamide, these strands are linked together at various spots along their length, making a much "tighter" network.

The average particle size of the microcapsules will generally range from about 3 to about 130 microns with a preferred average particle size of about 10 to 45 microns. Such relatively fine particles are advantageous to prevent plugging of orifices in the spraying equipment used for field application of the pesticide compositions.

The wall thickness of the cross-linked, polyamide-polyurea capsule will range from about 0.5 micron to 4 microns, with from about 1 to 3 microns thickness preferred. The thickness of the capsule wall, as well as the degree of crosslinking of the polymer constituting same, will affect the rate of diffusion of pyrethroid insecticide therethrough, and thereby influence the performance of the insecticide in the field relative to extended life and insect kill rate. The microcapsule size thereof is controlled during the manufacturing process by such expedients as carefully monitoring the degree of dispersion of the material to be encapsulated, by controlling the agitation and amount of emulsifying agent in the continuous phase. The microcapsule wall thickness is controlled by the quantity of the reactive intermediate dissolved in the material to be encapsulated.

A suspension or slurry of the microcapsules in water is the normal embodiment for shipping, storing, and ultimately dispensing the insectide composition to the urea to be protected from insect infestation. Conventional spraying apparatus is used for application of these insecticidal formulations.

EXAMPLE 1

The following solutions are prepared:

A. Stock solution of polyvinyl alcohol, a 4% aqueous solution of which has a viscosity of 35–45 cp. at 20° C. determined by Hoeppler falling ball method ("Elvanol 50-42 G," E. I. DuPont de Nemours & Company) in warm water with high speed stirring.

B. Amine solution of
  41.6 g. ethylene diamine
  4.76 g. diethylenetriamine
  0.56 g. sodium hydroxide in 25 cc. water
  200 ml. water C. Organic phase, prepared just prior to use.
  84.7 g. technical permethrin 94.4% active
  1.66 g. sebacyl chloride
  16.6 g. polymethylene polyphenylisocyanate ("PAPI 27," Upjohn Company)
  100.3 g. of Tenneco 500–100 ® aromatic solvent 500 ml. of 0.5% polyvinyl alcohol solution A is placed in a 1 liter baffled flask and stirred vigorously with a Kraft stirrer. The organic phase, solution C, is added, followed immediately by amine solution B. A paddle stirrer is substituted for the dispersion stirrer and the mixture is agitated slowly to maintain suspension for 2 hours. The resulting suspension is diluted with additional water and then sieved through a 50 mesh screen. The product is then neutralized to a pH of 7 and thickened with 0.3 g. of xanthan gum. A total of 1843 g. of slurry is obtained.

The resulting polyamide-polyurea capsules of the invention have the preferred properties as set forth in the Summary of the Invention and claims.

Utilizing the above described efficacy and fish toxicity tests, the results as shown in Tables I below are obtained.

Fish toxicity results illustrating the mortality of rainbow trout exposed to permethrin E.C. and permethrin encapsulate for 96 hours are shown in Table I (page 16) of the parent application Ser. No. 668,231, filed Nov. 5, 1984 (now abandoned).

TABLE I

| Formulation | Percent House Fly Mortality, After Initial 30 Day Aging Period After day: | | | | | | |
| --- | --- | --- | --- | --- | --- | --- | --- |
| | 1 | 3 | 7 | 14 | 28 | 56 | Mean |
| Microencapsulated permethrin sample of Example I. | 95 | 87 | 90 | 82 | 73 | 49 | 79 |
| Emulsifiable concentrate of permethrin | 84 | 89 | 95 | 82 | 51 | 17 | 70 |

Example I above can be repeated with the other pyrethroids, such as: allethrin, dimethrin, resmethrin, bioresmethrin, phenothrin, biopermethrin, decamethrin, fenvalerate, and barthrin (as well as with other known pyrethroids), with similar results.

The various examples of U.S. Pat. No. 3,577,515 (Vandegaer) can be repeated, except for substitution of each of the above pyrethroids, to provide polymeric shells or skins of polyamide, polysulfonamide, polyester, polycarbonate, polyurethane, polyurea, or polyamide-polyurea, with results similar to those of Example I.

It is thus apparent that the microencapsulated product of this invention has enhanced long term efficacy when compared to the conventional formulations of the same pyrethroid. Most surprisingly, the huge and unexplained decrease in fish toxicity with the product of the invention opens up entirely new fields of use for these important pyrethroids.

We claim:

1. In the art of applying a pyrethroid insecticide to fish-containing aquatic sites infested with insects, the improvement decreasing fish toxicity, consisting essentially of the step of contacting said fish-containing insect-infested aquatic site with a non-fish toxic effective insecticidal amount of a storage-stable, sprayable, aqueous-based insecticidal composition consisting essentially of a mixture in water of microcapsules comprised of a pyrethroid contained within an encapsulating wall of a cross-linked polymeric material selected from the group consisting essentially of polyamide-polyurea, polyamide, polysulfonamide, polyester, polycarbonate, polyurethane, and polyurea, the pyrethroid being diffusible therethrough, about 10 to 100% of the cross-linked polymeric encapsulating wall being embodied in a three dimensional polymer network, the weight ratio of said pyrethroid to the polymer of the microcapsule being in the range of about 1:1 to 50:1 and the concentration of the microcapsules in the aqueous mixture being from about 1 to about 50% by weight.

2. The composition of claim 1 wherein the average particle size of the microcapsules is within the range of about 3 to 130 microns.

3. The composition of claim 1 wherein about 20 to 90% of the cross-linked polymeric encapsulating wall is embodied in a three dimensional polymer network.

4. The composition of claim 1 wherein the pyrethroid is selected from the group consisting essentially of allethrin, dimethrin, tetramethrin, cypermethrin, resmethrin, bioresmethrin, phenothrin, permethrin, biopermethrin, decamethrin, fenvalerate, fluvalinate, and barthrin.

5. The composition as defined in claim 4 wherein the polymeric material is polyurea or polyamide-polyurea and the pyrethroid is permethrin or fenvalerate.

6. The method of reducing fish toxicity while controlling mosquitos in aquatic sites containing fish which comprises applying an insecticidally effective amount of the composition as defined in claims 1, 2, 3, 4, or 5 to water-containing fish in which the mosquitos and mosquito larvae breed, hatch, develop, and live.

* * * * *